United States Patent
Moore et al.

[11] Patent Number: 5,961,530
[45] Date of Patent: Oct. 5, 1999

[54] APPARATUS FOR ATTACHING SUTURE TO BONE

[75] Inventors: Robert R. Moore, Hayward, Calif.; Arnold K. Cohn, Glenview, Ill.

[73] Assignee: Orthopedic Systems, Inc., Union City, Calif.

[21] Appl. No.: 08/871,840

[22] Filed: Jun. 5, 1997

Related U.S. Application Data

[63] Continuation of application No. 08/326,047, Oct. 19, 1994, which is a continuation of application No. 08/049,089, Apr. 16, 1993, which is a continuation-in-part of application No. 07/895,604, Jun. 8, 1992, Pat. No. 5,250,055.

[51] Int. Cl.⁶ ..................................... A61B 17/04
[52] U.S. Cl. .......................... 606/148; 606/139; 606/205; 606/79
[58] Field of Search .................... 606/148, 205, 606/207, 11, 139, 144, 145, 147, 79, 86

[56] References Cited

U.S. PATENT DOCUMENTS

| | | | |
|---|---|---|---|
| 722,105 | 3/1903 | Hervey | 606/222 |
| 2,543,780 | 3/1951 | Hipps et al. | 606/86 |
| 2,725,053 | 11/1955 | Bambara | 606/96 |
| 4,545,374 | 10/1985 | Jackson | 606/17 |
| 4,590,929 | 5/1986 | Klein | 606/80 |
| 4,625,717 | 12/1986 | Covitz | 606/103 |
| 4,744,353 | 5/1988 | McFarland | 606/96 |
| 4,779,616 | 10/1988 | Johnson | 606/148 |
| 4,935,027 | 6/1990 | Yoon | 606/148 |
| 4,957,498 | 9/1990 | Caspari et al. | 606/144 |
| 5,026,350 | 6/1991 | Tanaka et al. | 604/164 |
| 5,037,422 | 8/1991 | Hayhurst et al. | 606/232 |
| 5,037,433 | 8/1991 | Wilk et al. | 606/222 |
| 5,054,501 | 10/1991 | Chuttani et al. | 604/282 |
| 5,102,421 | 4/1992 | Anspach, Jr. | 606/232 |
| 5,207,753 | 5/1993 | Badrinath | 606/96 |
| 5,257,637 | 11/1993 | El Gazayerli | 606/139 |
| 5,304,185 | 4/1994 | Taylor | 606/147 |
| 5,312,432 | 5/1994 | Pingleton et al. | 606/205 |
| 5,318,528 | 6/1994 | Heaven et al. | 604/95 |
| 5,342,390 | 8/1994 | Slater et al. | 606/205 |
| 5,383,877 | 1/1995 | Clarke | 606/148 |
| 5,387,221 | 2/1995 | Bisgaard | 606/148 |

FOREIGN PATENT DOCUMENTS

| | | | |
|---|---|---|---|
| 0166102 | 11/1964 | U.S.S.R. | 606/222 |
| 0172957 | 7/1965 | U.S.S.R. | 606/222 |
| 1115736 | 9/1984 | U.S.S.R. | 606/222 |

*Primary Examiner*—Michael Buiz
*Assistant Examiner*—Tina T. D. Pham
*Attorney, Agent, or Firm*—Limbach & Limbach

[57] ABSTRACT

An apparatus for use in arthroscopically attaching a suture to bone comprises a cannula and drill guide for use in drilling parallel holes in the bone and a scissors-like component for carrying a suture down one hole and pushing the suture through soft bone into the other hole where it can be retrieved.

8 Claims, 6 Drawing Sheets

APPARATUS FOR ATTACHING SUTURE TO BONE

This is a continuation of application Ser. No. 08/326,047, filed Oct. 19, 1994, which is a Continuation of application Ser. No. 08/049,089 filed Apr. 16, 1993, which is a Continuation-in-Part of application Ser. No. 07/895,604, filed Jun. 8, 1992, now U.S. Pat. No. 5,250,055.

BACKGROUND OF THE INVENTION

This invention relates to an apparatus for attaching sutures to bone and more particularly to doing so arthroscopically.

It is desirable to be able to attach a suture to bone with the suture encircling a portion of the hard material which forms the surface portion of the bone so that the strength of that hard portion of the bone forms a strong anchor for the suture. Apparatus for anchoring sutures in this way is sold by Orthopedic Systems Inc. under the name COHN Suture Fixation Device. That apparatus provides two intersecting drilled holes into the bone through which a suture can be passed, but it is not readily adapted to arthroscopic surgery because it requires that a large opening be made for access to the bone.

SUMMARY OF INVENTION

In accordance with this invention, a suture can be attached to the bone with the same final strength that is achieved with the COHN S.F.D. and the procedure may be performed arthroscopically. The procedure is performed by insertion of a small cannula to the bone through overlying soft tissue. A drill guide with at least two generally parallel bores is inserted in the cannula and used for drilling two parallel holes in the bone through the hard material near the surface of the bone down into the soft interior material of the bone. The two holes in the bone need not intersect.

A suture pusher is then inserted through one of the bores in the drill guide and operated to push a suture loop through the soft bone material from one hole to the other. At the tip of the suture pusher is a suture pushing end which is pivoted from one bore hole to the other using an actuating means. The suture pusher may take the form of a scissors-like device which has a set of scissors handles located at one end of a pair of parallel arms.

The suture pusher is provided with an eye to carry the suture or it may be provided with a notched end similar to that employed in the COHN S.F.D. When the suture pushing end is inserted through one hole and pivots to the other hole it carries the loop of the suture which may be retrieved with a hook through the second hole in the manner in which a suture is retrieved with a COHN S.F.D. Once the suture is in place extending into and out of the bone, the suture pusher and drill guide are withdrawn; knots may be tied in the suture and passed along the suture through the cannula to the bone; the ends of the suture are clipped off and the cannula is removed.

It may be possible to fix a suture using the drill guide alone without the cannula where the drill guide performs the function of the cannula, but it is preferred to use separate drill guides and cannulas so that knots can be passed down the suture to the bone while surrounding soft tissue is held back.

In this manner a suture can be attached to the bone firmly anchored by encircling the bridge of hard bone material between the two parallel drill holes, and the attachment is accomplished without leaving metal anchoring materials in the bone. The suture may be used for attaching any desired material to the bone as for instance where the end of a ruptured tendon may be initially held to the bone by the cannula and then attached to the bone by the suture.

DETAILED DESCRIPTION

In the accompanying drawings FIG. 1 is a side perspective view of the cannula with a schematic diagram of a shoulder to which a ruptured tendon is to be attached;

Figure 1:
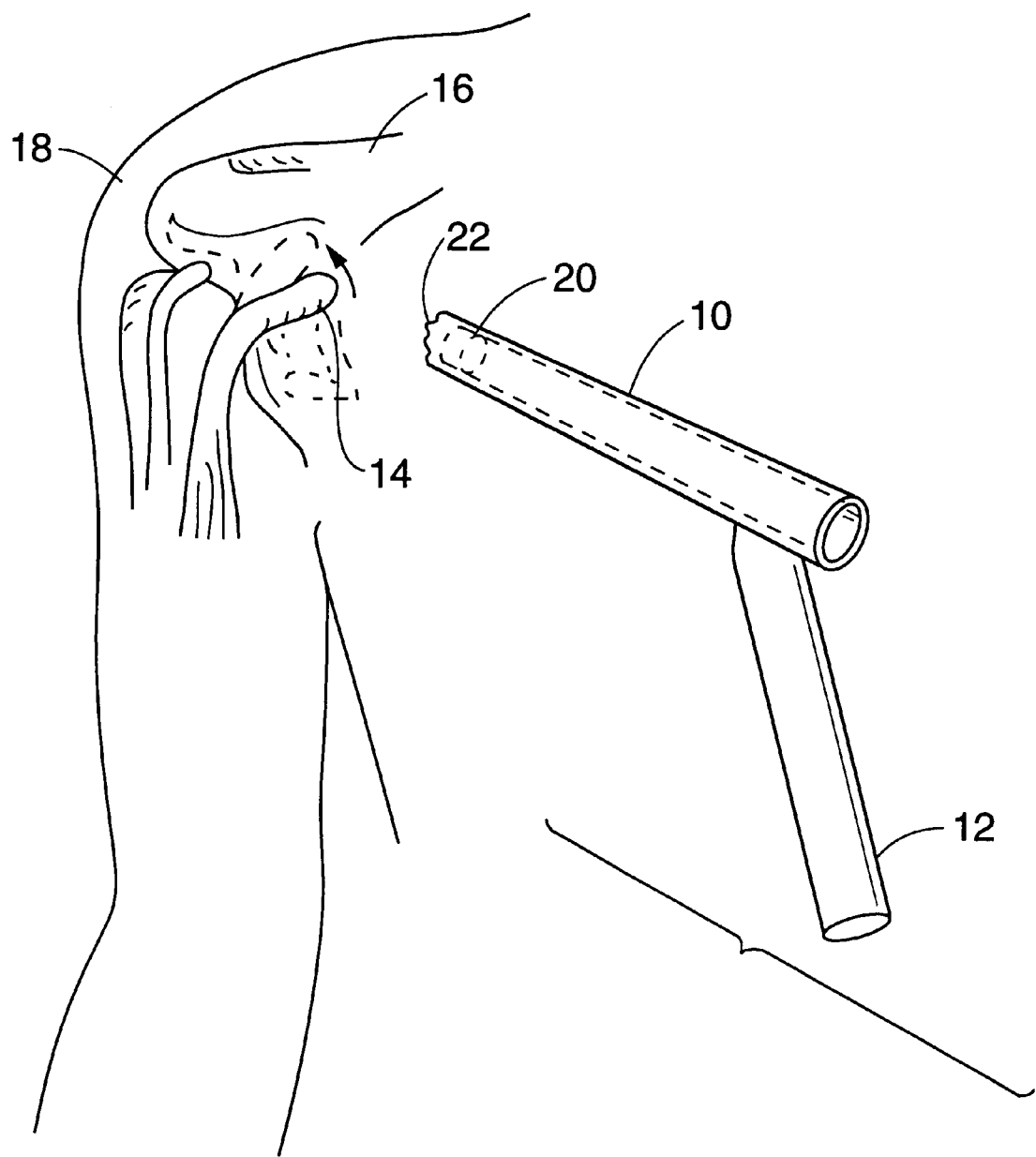
Figure 2:
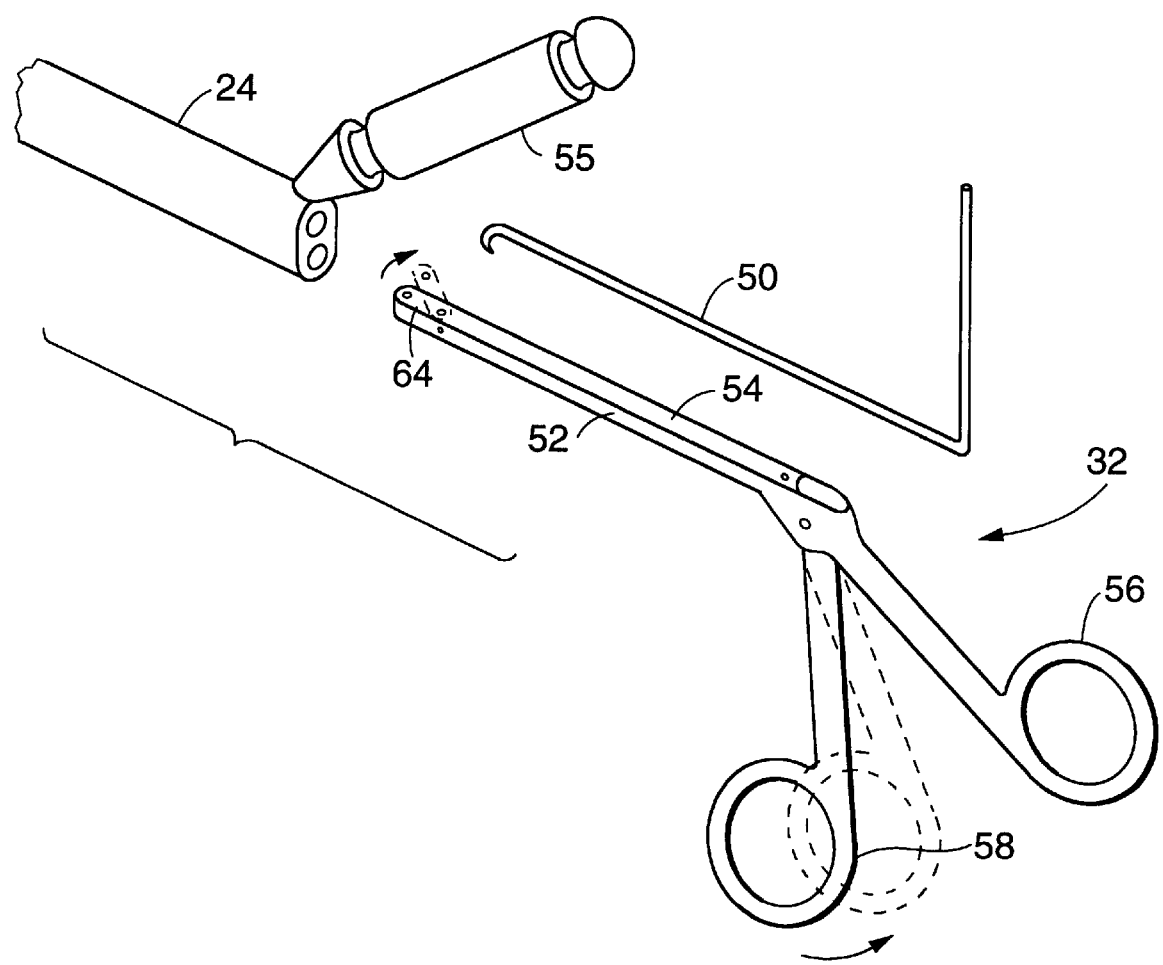
FIG. 2 is an exploded view of the apparatus of this invention.
Figure 3:
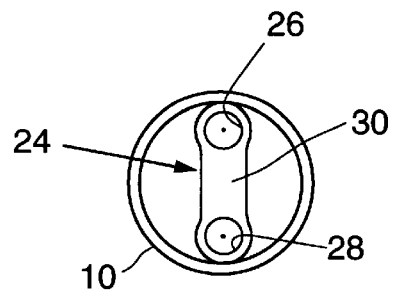
FIG. 3 is a cross sectional view of the cannula with the drill guide in place.
Figure 4:
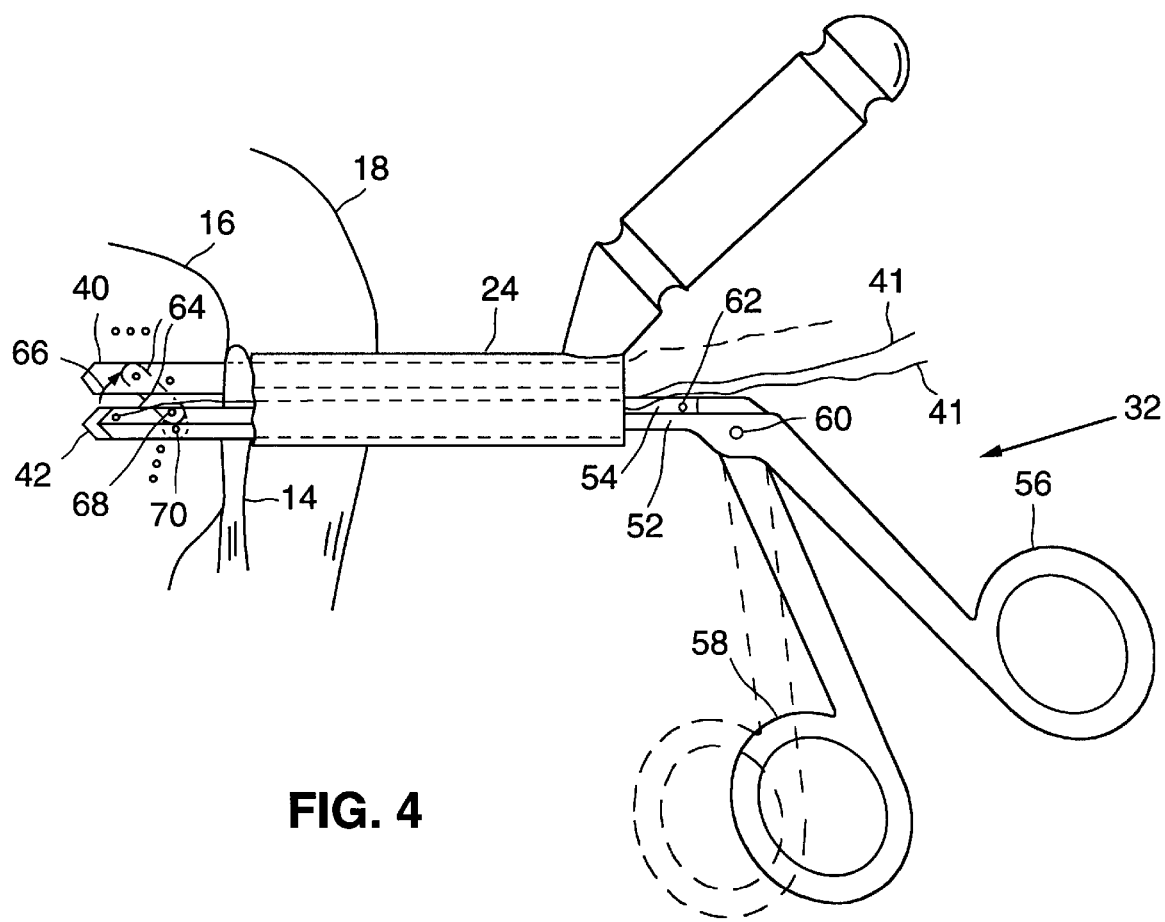
FIG. 4 is a side elevational view of the apparatus of this invention with all parts assembled.

Referring now in detail to the drawings and particularly to FIGS. 1, 2 and 3, a cannula 10 having a handle 12 is used to form a passageway for arthroscopic surgery to attach a tendon 14 to a bone 16 through overlying soft tissue 18.

The end of the cannula may contain a removable plug 20 to facilitate insertion of the cannula through the soft tissue, and the inner end of the cannula may contain teeth 22 by which the tendon 14 may be grasped by the cannula. A drill guide 24 has a handle 55 and contains two generally parallel bores 26 and 28 preferably ⅛ inch in diameter separated by a central web preferably 30 ⅛ inch in diameter.

The suture pusher 32, which is constructed somewhat like a rongeur or arthroscopic grabber, is comprised of a pair of scissors handles 56, 58 extending angularly from the distal ends of a pair of parallel arms 52, 54. A first embodiment of the suture pusher is shown in FIG. 4 and FIGS. 9 through 12.

Figure 9:
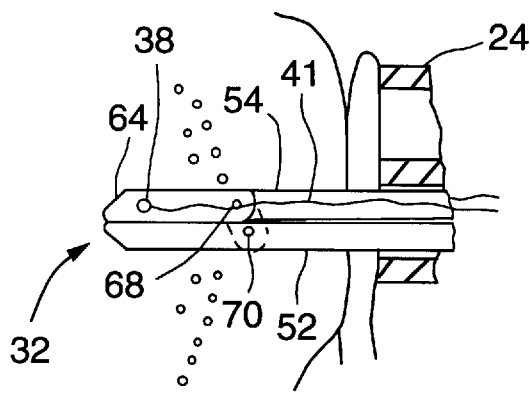
Figure 10:
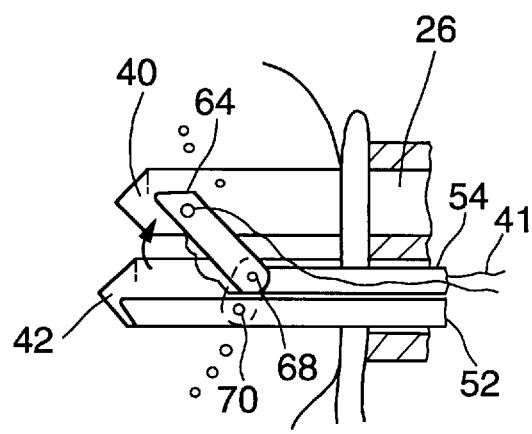

A suture pushing end 64 is connected to the proximal end of the parallel arms 52, 54. At the proximal end of the suture pushing end is an eye 38 through which a suture 41 is threaded as illustrated in FIG. 9. When the suture pushing member 64 is pivoted as described below, it carries the suture from one hole in the bone to the other as shown in FIG. 10. The distal end of the suture pushing end connects to parallel arm 52 at fixed pivot 70.

The suture pusher 32 of the first embodiment has four essential pivot points. Fixed pivot 60 joins scissors handles 56, 58 at their point of intersection. Parallel arm 54 is connected to scissors handle 58 at pivot 62 on the distal end and is connected to suture pushing end 64 at pivot 68. Fixed pivot 70 joins suture pushing end 64 to parallel arm 52.

To pivot the suture 41 from the first hole 42 to the second hole 40, scissors handle 58 is pivoted away from scissors handle 56 around fixed pivot 60. This causes parallel arm 54 to slide in the distal direction, towards the scissors handles, thereby pulling on suture pushing end 64 at pivot point 68. The suture pushing end 64 pivots about fixed pivot 70, carrying the suture 41 into the second hole 40.

Figure 5:
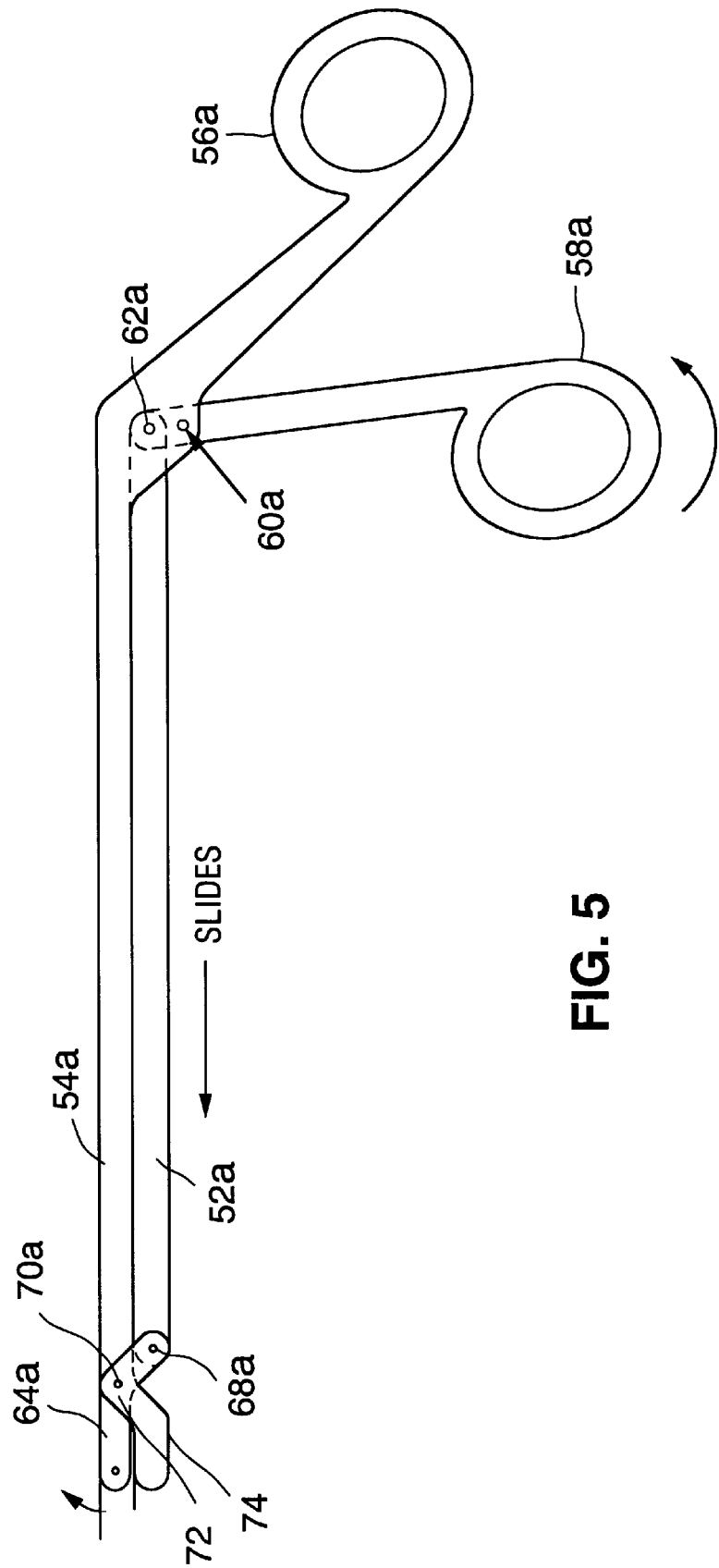
FIG. 5 is a side schematic representation of an alternative embodiment of the suture pusher of this invention.

FIG. 5 is a schematic side representation of an alternative embodiment of the suture pusher. This embodiment is quite similar to the first embodiment but may be preferred because it allows the surgeon to pivot the suture from the first hole into the second hole by closing the scissors handles rather than by opening them.

A pair of scissors handles 56a, 58a extends angularly from the distal ends of a pair of parallel arms 52a, 54a.

Scissors handles 58a and 56a are joined by fixed pivot 60a, and scissors handle 58a is connected to parallel arm 52a at pivot 62a. At its proximal end, parallel arm 52a is attached to suture pushing end 64a at pivot point 68a. Fixed pivot 70a joins parallel arm 54a to suture pushing end 64a.

The proximal end of parallel arm 54 has a downwardly angled portion 72 which extends from the parallel arm at an obtuse angle and joins a second parallel portion 74 at the proximal end of the angled portion 72. The second parallel portion 74 of parallel arm 54a is parallel to the proximal portion of the suture pushing end 64a.

To use the alternative embodiment of the suture pusher, scissors handle 58a is pivoted around fixed pivot 60a in a distal direction, moving towards scissors handle 56a. This causes parallel arm 52a to slide in a proximal direction, thereby pushing suture pusher 64a at pivot 68a and causing the suture pushing end 64a to pivot around fixed pivot 70a. The suture (not shown) is thereby carried by the eye 38 into the second hole (not shown).

Figure 6:
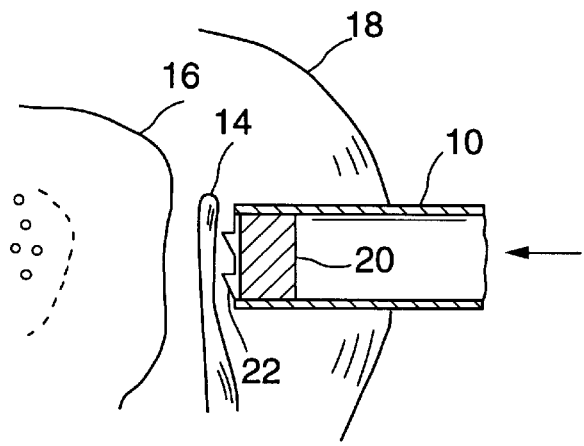
FIGS. 6 through 12 are a series of figures showing the sequence of steps performed in accordance with the invention.
Figure 7:
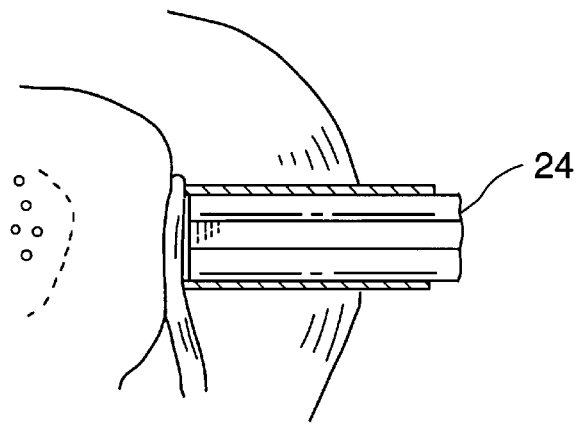
Figure 8:
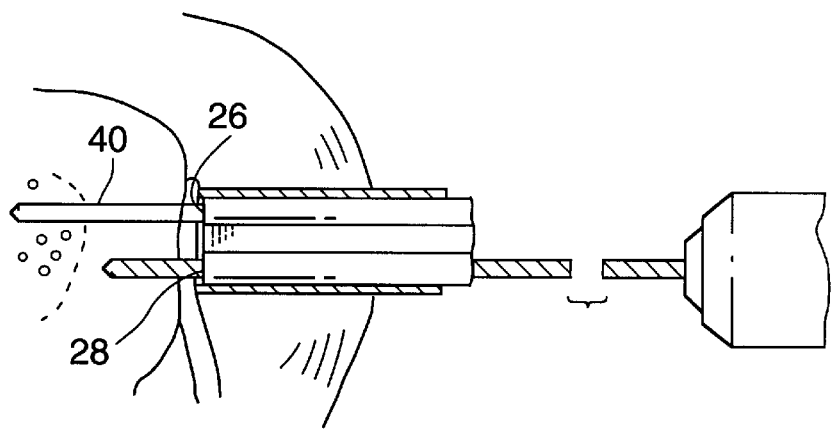

As explained above this apparatus is used as follows: The cannula 10 is inserted into the tissue as illustrated in FIG. 6 until it engages the bone where a suture is to be attached. Where the tendon 14 is to be attached to the bone by the suture the tendon is grasped and held to the bone by the cannula as the cannula is inserted and the drill guide 24 is then inserted as shown in FIG. 7. A drill is then used as shown in FIG. 8 to drill two holes 40 and 42 aligned with the bores 26 and 28 respectively of the drill guide.

A suture 41 is then threaded through the eye 38 in the suture pusher 32 and the suture pusher is forced into the bore 28 of the drill guide and into the hole 42, such that the two parallel arms 52 and 54 extend through one bore of the drill guide 24 as shown in FIG. 9. Pivoting scissors handle 58 around pivot pin 60 as described above causes the suture pushing end 64 to push the suture 41 from one hole 42 to the other hole 40.

Figure 11:
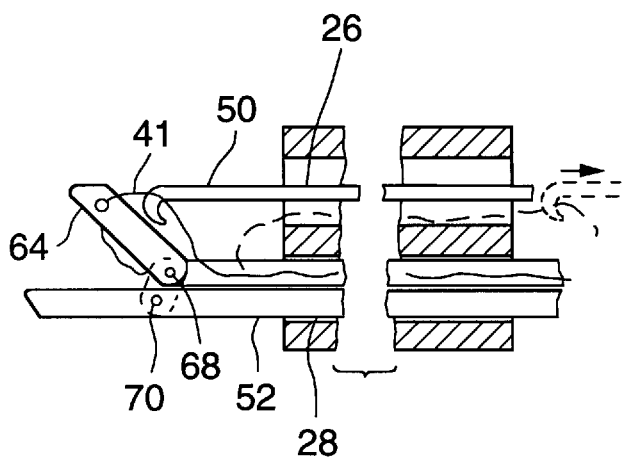

Once the suture pushing member 64 penetrates from the hole 40 to the hole 42 as illustrated in FIGS. 10 and 11, one end of the suture may be retrieved through the drill bore 26 by a suitable suture hook 50 as shown in FIG. 11.

Figure 12:
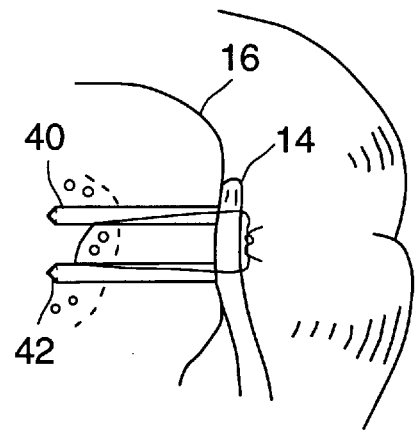

Finally once the suture has been retrieved out through the bore 26, the suture pusher and the drill guide may be withdrawn. Knots are then tied in the suture and passed down the cannula to attach the tendon 14 to the bone 16, and the excess ends of the suture may be cut off and the cannula withdrawn leaving the suture attached as shown in FIG. 12.

While certain details of the invention have been illustrated and described herein it is obvious that many modifications thereof may be made.

We claim:

1. An instrument set for use in pushing a suture from a first hole in bone to a second hole in bone, the instrument set comprising:
    a suture pusher including
        a primary arm having a distal end insertable through a first hole in bone,
        a secondary arm mounted on the primary arm for generally longitudinal movement with respect thereto, and
        a suture pushing member having an opening in its distal portion for receiving a suture, the suture pushing member pivotally connected to the primary arm near the distal end thereof and connected to the secondary arm to be pivoted from a retracted position to a laterally projected position responsive to movement of the secondary arm longitudinally of the primary arm and to thereby push a portion of a suture carried by the aperture from the first hole to a second hole in the bone; and
    suture-retrieving means extendable through the second hole and having a suture engaging element at its distal end for retrieving a portion of the suture from the second hole.

2. The instrument set of claim 1 wherein the suture pushing member is pivotally connected at one end to the secondary arm and at an intermediate point to the primary arm.

3. An instrument set for use in pushing a suture from a first hole in bone to a second hole in bone, the instrument set comprising:
    a cannula having a tissue engaging end;
    a suture pusher including
        a primary arm having a distal end insertable through the cannula and through a first hole in bone,
        a secondary arm mounted on the primary arm for generally longitudinal movement with respect thereto, and
        a suture pushing member having an opening at its distal portion for receiving a suture, the suture pushing member pivotally connected to the primary arm near the distal end thereof and connected to the secondary arm to be pivoted from a retracted position to a laterally projected position responsive to movement of the secondary arm longitudinally of the primary arm and to thereby push a portion of a suture carried by the aperture from the first hole to a second hole in the bone; and
    suture-retrieving means extendable through the cannula and the second hole and having a suture engaging element at its distal end for retrieving a portion of the suture from the second hole.

4. The instrument set of claim 3 wherein the tissue engaging end of the cannula includes at least one tooth engageable with tissue when pressed into contact with tissue.

5. The instrument set of claim 3 wherein the cannula is a drill guide having a pair of parallel bores.

6. The instrument set of claim 5 wherein the tissue engaging end of the drill guide includes at least one tooth engageable with tissue when pressed into contact with tissue.

7. An instrument set for attaching a suture to bone under soft tissue comprising:
    a drill guide having at least two generally parallel bores a distal end, and a barb on the distal end of the drill guide,
    a suture pusher having a straight section extendable through a first one of the bores in the drill guide and a suture carrying member at the distal end of the suture pusher, the suture carrying member pivotable to push a suture loop through soft bone material between first and second parallel holes in the bone, the suture carrying member including an opening for receiving a suture,
    an actuator positioned at the proximal end of the suture pusher, for pivoting the suture carrying member from the first to the second of the two parallel holes while the suture pusher is received in the drill guide, and
    a suture-retriever extendable through a second one of the bores in the drill guide, for retrieving a portion of the suture from the second of the two parallel holes in the bone.

8. The instrument set of claim 7 further comprising a cannula capable of receiving the drill guide.

* * * * *